United States Patent
Kroll

[11] Patent Number: 6,132,426
[45] Date of Patent: Oct. 17, 2000

[54] TEMPERATURE AND CURRENT LIMITED ABLATION CATHETER

[75] Inventor: Mark W. Kroll, Minnetonka, Minn.

[73] Assignee: Daig Corporation, Minnetonka, Minn.

[21] Appl. No.: 09/072,945

[22] Filed: May 5, 1998

[51] Int. Cl.$^7$ .................................................. A61B 18/18
[52] U.S. Cl. ................................ 606/41; 606/29; 606/34; 607/101
[58] Field of Search .................. 606/27–31, 41, 606/42, 45–50; 607/98–102

[56] References Cited

U.S. PATENT DOCUMENTS

| | | |
|---|---|---|
| 3,768,482 | 10/1973 | Shaw .......................................... 606/45 |
| 4,641,649 | 2/1987 | Walinsky et al. . |
| 4,945,912 | 8/1990 | Langberg . |
| 5,122,137 | 6/1992 | Lennox . |
| 5,209,229 | 5/1993 | Gilli . |
| 5,228,442 | 7/1993 | Imran . |
| 5,231,995 | 8/1993 | Desai . |
| 5,242,441 | 9/1993 | Avitall . |
| 5,246,438 | 9/1993 | Langberg . |
| 5,263,493 | 11/1993 | Avitall . |
| 5,281,213 | 1/1994 | Milder et al. . |
| 5,281,217 | 1/1994 | Edwards et al. . |
| 5,281,218 | 1/1994 | Imran . |
| 5,293,868 | 3/1994 | Nardella . |
| 5,571,153 | 11/1996 | Wallsten .................................... 607/98 |
| 5,611,798 | 3/1997 | Eggers et al. ............................. 606/31 |
| 5,693,080 | 12/1997 | Wallsten et al. ......................... 607/105 |
| 5,697,909 | 12/1997 | Eggers et al. ........................... 604/114 |
| 5,891,134 | 4/1999 | Goble et al. .............................. 606/27 |

OTHER PUBLICATIONS

*Basic Aspects of Radiofrequency Catheter Ablation*, Sunil Nath, M.D., John P. DiMarco, M.D., Ph.D., and David E. Haines, M.D., from the Cardiovascular Division, Dept. of Internal Medicine, University of Virginia Health Sciences Center, Charlottesville, Virginia, pp. 863–876, Sep. 1994.

*EP–Shuttle*, User Manual, Cordis Webster, pp. 1–81, Jan. 31, 1997.

*RFG–3D Lesion Generator*, Operator's Manual, Radionics, Inc., Rev. C, pp. A–10, May 3, 1996.

Primary Examiner—Michael Peffley
Attorney, Agent, or Firm—Scott R. Cox

[57] ABSTRACT

An ablation catheter of the present invention includes a means for limiting a current and temperature at a target tissue site. The ablation catheter includes a tip electrode at its distal end, and a positive temperature coefficient (PTC) device between the distal end and a proximal end of the catheter. Both the PTC device and electrode are electrically connected via a conductor extending within the catheter.

4 Claims, 5 Drawing Sheets

TEMPERATURE AND CURRENT LIMITED ABLATION CATHETER

FIELD OF THE INVENTION

The present invention relates to ablation catheters. In particular, the present invention relates to a temperature and current limited ablation catheter.

BACKGROUND OF THE INVENTION

Ablation catheters are well recognized and important tools for conveying an electrical stimulus to selected locations within the human body. Ablation catheters have been used for many years for the treatment of certain types of cardiac arrhythmia. For example, ablation catheters have been used to interrupt or modify existing conduction pathways associated with arrhythmias within the heart. Ablation procedures are also used for the treatment of atrial ventricular (AV) nodal reentrant tachycardia. Accepted treatments of this condition include ablation of the fast or slow AV nodal pathways. Known cardiac ablation procedures focus on the formation of lesions within the chambers of the heart at selected locations which will either prevent the passage of electrical signals associated with atrial premature contractions or prevent the formation of improper electrical pathways within the heart which can result in atrial arrhythmia.

Radio frequency (RF) catheter ablation has become increasingly popular for many symptomatic arrhythmias such as AV nodal reentrant tachycardia, AV reciprocating tachycardia, idiopathic ventricular tachycardia, and primary atrial tachycardias. Nath, S., et al., "Basic Aspects Of Radio Frequency Catheter Ablation," *J Cardiovasc Electrophysiol*, Vol. 5, pgs. 863–876, October 1994. RF ablation is also a common technique for treating disorders of the endometrium and other body tissues including the brain.

A typical RF ablation system in its most basic form comprises an RF generator which feeds current to a catheter containing a conductive tip electrode for contacting targeted tissue. The system is completed by a return path to the RF generator, provided through the patient and a large conductive plate, which is in contact with the patient's back.

The standard RF generator used in catheter ablation produces an unmodulated sine wave alternating current at frequencies of approximately 500 to 1000 kHz. The RF energy is typically delivered into the patient between the conductive tip electrode of the catheter and the large conductive plate in contact with the patient's back. During the delivery of the RF energy, alternating electrical current traverses from the conductive tip through the intervening tissue to the back plate. The passage of current through the tissue results in electromagnetic heating. Heating tissue to temperatures above 50° C. is required to cause irreversible myocardial tissue injury. However, heating tissue to temperatures above approximately 100° C. at the electrode/tissue interface can result in boiling of plasma and adherence of denatured plasma proteins to the ablation electrode. The formation of this coagulum on the catheter tip causes a rapid rise in electrical impedance and a fall in the thermal conductivity, resulting in loss of effective myocardial heating. Nath, S., et al., "Basic Aspects Of Radio Frequency Catheter Ablation," *J Cardiovasc Electrophysiol*, Vol. 5, pgs. 863–876, October 1994. Moreover, such extreme heating of the tissues can damage healthy tissue surrounding the targeted lesion.

Because of the dangers of overheating tissue with ablation catheters, systems for controlling the temperature at the ablation site are necessary. Such systems have been in use for many years. Common ablation systems for controlling the temperature at the ablation site contain an electrode as well as a thermocouple or thermistor at the tip of the catheter. In these systems, a pair of wires from the thermocouple extend back through the body of the catheter to an amplifier in an electrical control portion of the system. An output from the amplifier, is indicative of the temperature of the heated tissue and is used by a control unit to control the duty cycle or power level of the RF generator. This arrangement permits regulating the amount of RF energy delivered to the tissue to control the temperature at the target tissue. An example of a system in which the duty cycle of the ablation catheter is controlled by a temperature sensor is disclosed in U.S. Pat. No. 5,122,137 entitled "Temperature Controlled RF Coagulation."

Known RF ablation systems that use temperature control mechanisms have numerous disadvantages. First, additional wires are required for the connection to the thermocouple. Each additional wire is a reliability and manufacturing problem when constructed in a long, thin catheter. Second, the transmission of a low voltage signal from the thermocouple to the amplifier, which is indicative of the temperature, must be transmitted accurately over a long distance in order to appropriately limit the temperature. Maintaining an accurate transmission is very difficult because the low voltage signals from the thermocouple are being transmitted by wires directly adjacent the wire used to provide the high voltage signal for ablating. The low voltage signals from the thermocouple are typically swamped by the high voltages and high frequencies used for the ablation, thereby causing temperature signals to be very noisy and less likely to give accurate temperature readings. Finally, in the event of an electronics fault, there is no mechanism in the known devices for current limiting or fusing capability to protect the patient and/or catheter.

SUMMARY OF THE INVENTION

An ablation catheter of the present invention includes a means for limiting the current and temperature at a target tissue site. The ablation catheter includes a tip electrode at its distal end, and a positive temperature coefficient (PTC) device between the distal end and a proximal end of the catheter. Both the PTC device and electrode are electrically connected via a conductor extending within the catheter.

The PTC device limits a current flowing to the electrode according to an exponential temperature and resistance relationship of the PTC device. Accordingly, when the temperature of the PTC device reaches a specified level, the PTC device becomes extremely resistive. This reaction effectively limits the current delivered to the target tissue and thereby ultimately limits the temperature of the target tissue by decreasing the amount of ablative RF energy directed to the target tissue.

DETAILED DESCRIPTION OF THE PREFERRED EMBODIMENT

Figure 1:
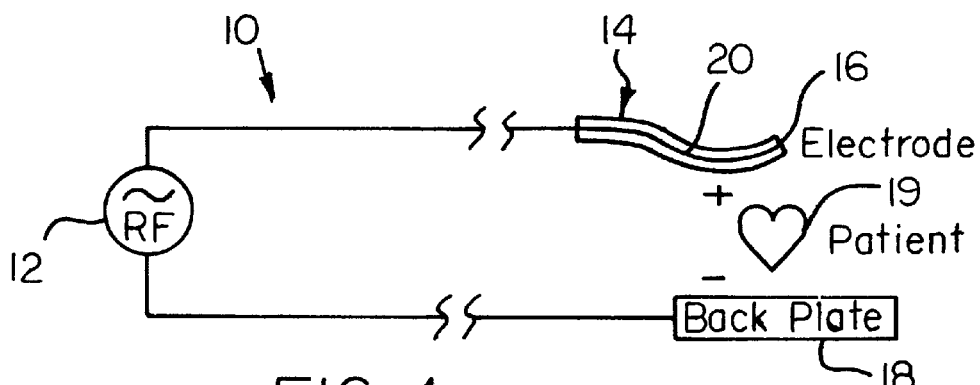
FIG. 1 is a schematic drawing of a basic known RF ablation catheter system.

The present invention includes a temperature and current limited ablation catheter. As previously stated, ablation catheters are well recognized and important tools for conveying an electrical stimulus to selected locations within the human body. FIG. 1 illustrates a schematic drawing of a known basic RF ablation catheter system 10. System 10 includes an RF signal generator 12, a catheter 14, a tip electrode 16 and a backplate 18. An electrical conductor 20 within catheter 14 extends between and electrically connects electrode 16 to RF generator 12. In operation, RF generator 12 feeds a current to catheter 14 via conductor 20. During the delivery of RF energy, alternating electrical current traverses from tip electrode 16 through the intervening tissue 19 of the patient to backplate 18. The passage of current through the tissue results in resistive (joule) heating. When using an ablation system, the targeted tissue must be heated to temperatures above approximately 50° C. for effective ablation. However, temperatures at and above approximately 100° C. at the electrode/tissue interface can result in boiling of plasma and adherence of denatured plasma proteins to the ablation electrode. The formation of the coagulum on the catheter tip causes a rapid rise in electrical impedance and a fall in the thermal conductivity resulting in loss of effective myocardial heating. Because of the dangers of overheating tissue with ablation catheters, systems for controlling the temperature at the ablation site are necessary and such systems have been in use for many years.

Figure 2:
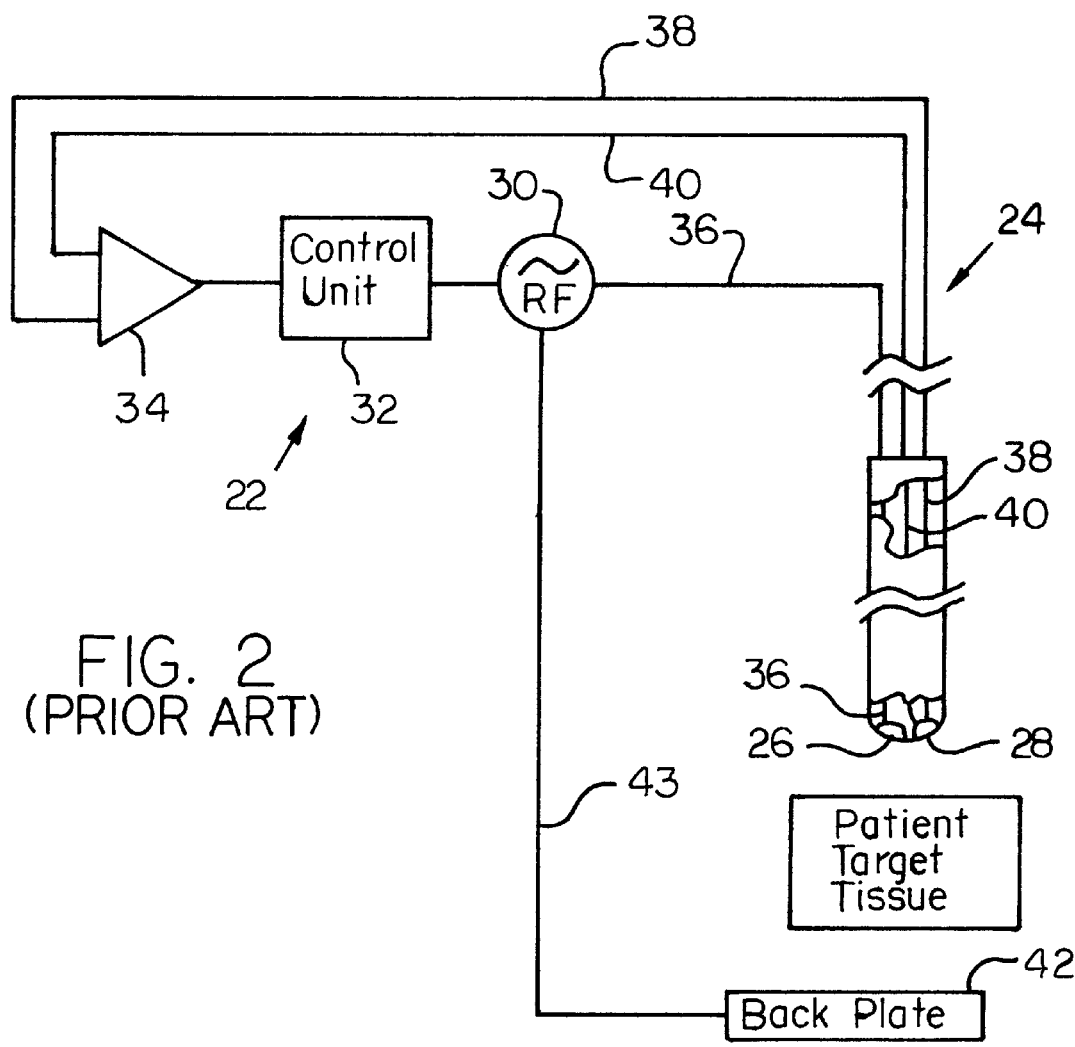
FIG. 2 is a schematic drawing of a known temperature controlled RF ablation catheter system.

FIG. 2 illustrates a known ablation system 22 for controlling the temperature at an ablation site. Ablation system 22 contains a catheter 24 having a tip electrode 26 and a thermocouple 28 connected to the distal end of catheter 24. System 22 also includes an RF generator 30, a control unit 32 and an amplifier 34. Electrode 26 is connected to RF generator 30 through a conductor 36. Thermocouple 28 is connected to RF generator 30 through control unit 32 and amplifier 34 via a pair of conductors 38, 40. A backplate 42 is also connected to RF generator 30 via conductor 43 to provide a return path for the current. In system 22, the output from amplifier 34 is indicative of the temperature sensed by thermocouple 28 and is used by control unit 32 to control the duty cycle or power level of RF generator 30. Despite this temperature control arrangement, this known ablation system may fail to optimally regulate temperatures at the target tissue due to the possibility of: (1) reliability/manufacturing problems; (2) inaccurate temperature signal transmission; and (3) a lack of other limits on the RF energy provided to the tissue.

Figure 3:
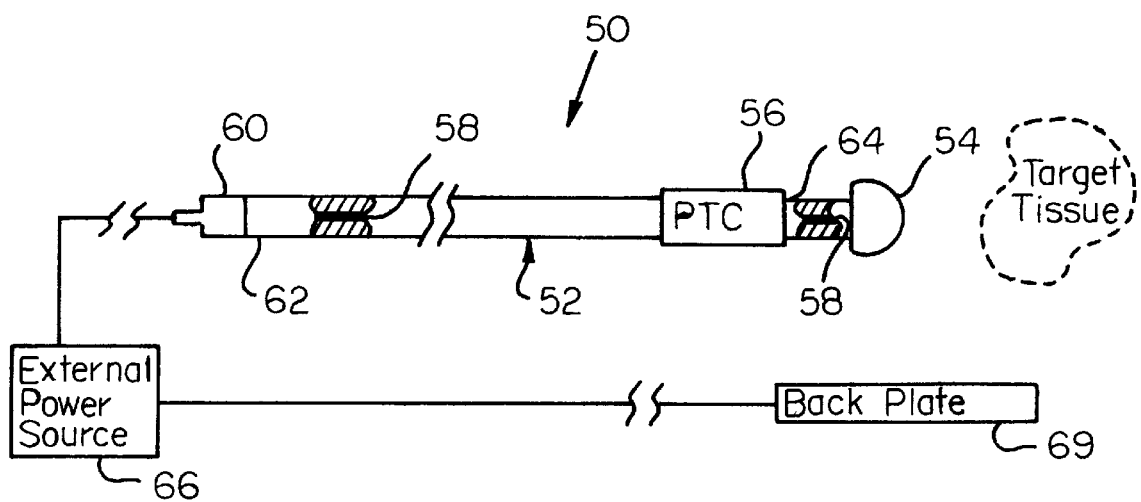
FIG. 3 is a schematic drawing of a temperature and current limited ablation catheter according to the present invention.

The present invention provides a radio frequency ablation catheter using a positive temperature coefficient (PTC) device in series with an electrode to provide a current limited and temperature limited device. FIG. 3 is a schematic drawing of a temperature and current limited ablation catheter 50 according to one preferred embodiment of the present invention. Catheter 50 includes a flexible body 52, a tip electrode 54 and a positive temperature coefficient (PTC) device 56, as well as a conductor 58, and a connector 60.

Flexible body 52 extends from the proximal end 62 to the distal end 64 of catheter 50. The composition of flexible body 52 is known to those skilled in the art. Catheter body 52 should be sufficiently pliable to permit the catheter to be advanced through the vascular system of the patient, for example, into the heart and ultimately into a pulmonary vein. In one embodiment of the present invention, the distal portion of catheter body 52 may be more pliable and less stiff than the remaining proximal portions of the catheter to assist the catheter in the advancement throughout the body. However, the pliability of catheter body 52 may also be consistent throughout its entire length. Additionally, catheter body 52 may be reinforced, for example, by use of a reinforcing braid or other such suitable strand material having high temporal strength.

Tip electrode 54 is connected to distal end 64 of catheter 50. Tip electrode 54 is used to deliver current from an external power source 66 to the tissue to be ablated. Tip electrode 54 is a standard tip electrode known to those skilled in the art. The single conductor 58 extends from proximal end 62 to distal end 64 within flexible body 52. Conductor 58 conducts the current from external power source 66 to tip electrode 54. The current loop is completed through the patient and back plate 69. Connector 60 is optionally provided at proximal end 62 to ease connection between conductor 58 and external power source 66. In the preferred embodiment of the present invention, external power source 66 is an RF generator, and reference will be made to an RF generator from hereout.

RF generators are known in the art. Examples include the EPT-1000™ from E.P. Technologies, the EP-Shuttle™ manufactured by Stockert GmbH and the RFG-30™ from Radionics, Inc. These devices typically produce radio frequency signals in the 500–1000 kHz range with power levels in the 0–100 watt range. These devices also have minimum and maximum impedance cut off ranges. For example, the EPT-1000™ has a pre-set 300 Ω maximum impedance cut off and a pre-set 50 Ω minimum impedance cut off. The maximum impedance cut off is to alert the operator, for example, that the catheter is broken and therefore there is an open circuit. The minimum impedance cut off is to alert the operator, for example, that there is a short circuit somewhere. The EP-Shuttle™ by Stockert has operator selectable maximum and minimum impedance cut off ranges. The maximum impedance is selectable between 50 and 300 Ω while the minimum impedance is selectable between 20 and 200 Ω. The EP-Shuttle™ also has an operator selectable maximum change in impedance (Δ) setting, selectable between 1–999 Ω.

In the present invention, positive temperature coefficient (PTC) device 56 is connected in series between proximal end 62 of catheter body 52 and tip electrode 54. PTC device 56 acts as an intrinsic fail-safe current limiting device. In the embodiment illustrated in FIG. 3, PTC device 56 is positioned adjacent tip electrode 54 but is not in thermal contact with electrode 54. In the embodiment illustrated, PTC device 56 is positioned approximately 5 cm from distal end 64. This is done for ease of construction. It should be noted, however, that PTC device 56 could be positioned anywhere between power source 66 and tip electrode 54 as will be described in greater detail below.

As previously stated, PTC devices are known as positive temperature coefficient devices. A known technique for making a PTC device is to use a very thermally expansive polymer that is blended with conductive materials. In this case, at low operating temperatures, the device may have very low resistance, typically less than 1 ohm. When a high current flows through the device, the device will begin to heat from joule heating. The increased temperature will cause an expansion of the polymer and change it to an amorphous state. This change separates the conductive paths within the polymer and causes a dramatic increase in the device resistance. The device resistance can change by a factor of 10,000,000 to 1 before the device fails. This dramatic response is illustrated by the graph in FIG. 4, which illustrates a sample resistance and temperature performance relationship of a positive temperature coefficient device.

Figure 4:
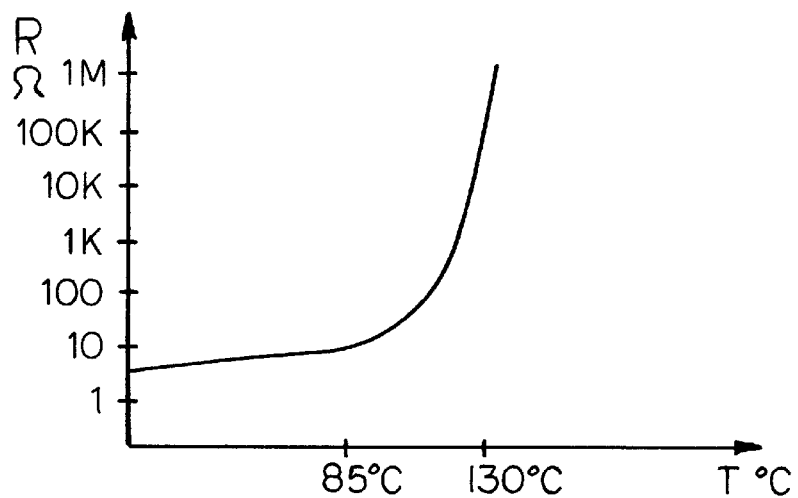
FIG. 4 is a graph illustrating a resistance and temperature performance relationship of a positive temperature coefficient (PTC) device of the present invention.

It should be understood that the resistance/temperature relationship shown in FIG. 4 is only shown as an example of one configuration of a PTC device. This relationship may be altered and tailored to the user's specifications depending upon the size, shape, and type of PTC device used. For example, the PTC device can be designed to have the rapid rise in resistance occur at approximately 130° C. as in FIG. 3, or to have it occur at greater or lesser temperatures. This gives great flexibility in designing current and temperature limited ablation systems.

One known PTC device is made by the Raychem Corporation of California under the brand name PolySwitch® Rxe. This Raychem model is not reactive (having no internal capacitance), permitting the polymer PTC device to function well at higher radio frequencies typically used for ablation. However, another known PTC device is made by the Siemens Matsushita Component Company, which has a ceramic construction well suited for limiting currents at moderate temperatures. Other PTC devices also may be used without departing from the spirit or scope of the present invention.

In operation, RF current is delivered from RF generator 66 through conductor 58 of catheter 50 to tip electrode 54. With tip electrode 54 in contact with the target tissue within the heart (or other portion of the vascular system), the RF power is delivered to the target tissue with the system circuit being completed through conductive backplate 69. RF power is supplied through tip electrode 54 to cause the target tissue to heat to a temperature of between 50° C. and 100° C. Heating the target tissue into the desired ablating range requires the application of substantial current through PTC device 56 to tip electrode 54. As the required current level increases, PTC device 56 begins to change to an amorphous state, thus increasing its resistance. It must be remembered that the resistance/temperature relationship depends upon the size, shape and type of PTC device selected. Using the relationship illustrated in FIG. 3, at current levels required to achieve ablation temperatures above 100° C., an ultra-high resistance is exhibited by PTC device 56. During the period of time in which PTC device 56 is changing from low resistance to high resistance, the current to electrode 54 is being reduced to effectively limit the current to electrode 54. Once the resistance of PTC device 56 is high enough, the maximum impedance cut off, or the maximum change in impedance cut off for the EP-Shuttle™, will be triggered causing RF generator 66 to stop outputting the RF signal. Thus, the current is limited. This also limits the temperature at the target tissue. By properly selecting the PTC device characteristics, the temperature at the target tissue may be maintained below 100° C. RF generator 66, will stay off until PTC device 56 has cooled down such that its resistance drops into an acceptable range. Cooling is provided by the rapidly flowing blood in the vascular system. Maintaining the temperature below 100° C. by using PTC device 56 prevents the boiling of plasma and the adherence of denatured coagulum to tip electrode 54 which would otherwise inhibit effective ablation.

Catheter 50 of the present invention provides a simple, elegant solution with numerous advantages. First, the use of PTC device 56 allows temperature limiting or regulation of ablation catheter 50 at tip electrode 54 by the use of only a single conductor 58 as opposed to a common three wire configuration that extends through prior art systems such as that shown in FIG. 2 to support a thermocouple. Moreover, since PTC device 56 need not be placed directly adjacent to tip electrode 54, the distal end of the catheter can be of a smaller design or of a design having different configurations not limited by the presence of a thermocouple. As previously stated, the particular tissue temperature at which PTC device 56 increases its resistance exponentially can be selected based upon the type and amount of power used so that a predetermined temperature range can be identified at which PTC device 56 limits the current and limits the temperature for ablation.

In addition to eliminating or reducing the extra number of wires that would be necessary to support a thermocouple-based temperature limiting system, catheter 50 of the present invention using PTC device 56 also provides a fusing-type capability for catheter 50 by virtue of its current limiting. Because of the current limiting capacity, a patient and/or catheter 50 is protected in the event of an electronics fault in the control unit or external power source which might otherwise cause the current to pass, or increase without constraint. Utilizing a single conductor wire in conjunction with a PTC device also eliminates the necessity for a feedback loop for monitoring and gauging the accuracy of a temperature signal from a thermocouple. Once the PTC device is selected for the desired predetermined temperature range at which it will limit the current, then a feedback loop for monitoring the temperature of the tip electrode is no longer necessary.

In one alternative embodiment of the present invention, PTC device 56 is insulated from the ambient conditions (e.g., surrounding vasculature and blood flow). In this embodiment, when PTC device 56 heats up from an over-current situation it does not cool down. This response results in a permanent/effective shut down of ablating the target tissue for two reasons. First, because of the high impedance of PTC device 56, RF generator 66 would shut down. Second, even if RF generator 66 did not have a maximum impedance cut off feature, the current passing through tip electrode 54 would be limited as to no longer effectively ablate the tissue. In this embodiment, PTC device 56 acts as a fail-safe feature thereby protecting catheter 50 and the target tissue while alerting the operator to investigate the ablation shut down.

Figure 5:
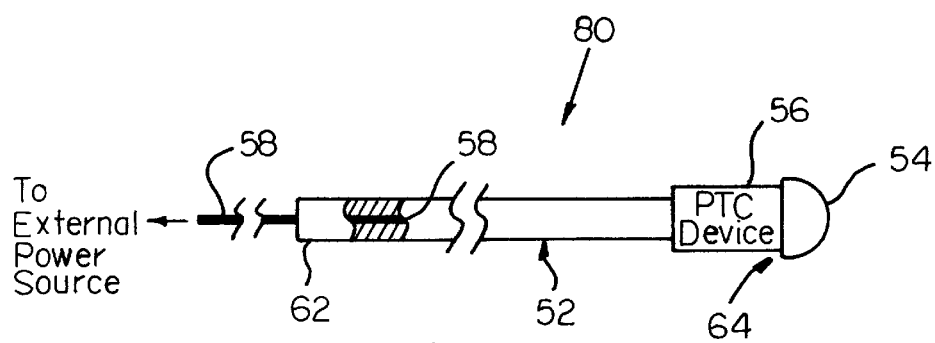
FIG. 5 is an alternative embodiment of a temperature and current limited ablation catheter according to the present invention.

In another embodiment of the present invention, a catheter 80 includes substantially the same features and structures as catheter 50 except that PTC device 56 is in mechanical and/or thermal contact with tip electrode 54. Thermal contact can be established by direct physical contact as shown in FIG. 5 or by other means known to those skilled in the art for providing thermal connectivity and conductivity between two devices such as PTC device 56 and tip electrode 54. By establishing thermal contact between PTC device 56 and tip electrode 54, catheter 80 has enhanced temperature limiting/shut off features in addition to the current limiting features provided by PTC device 56.

Accordingly, in this embodiment, PTC device 56 is no longer a pure current sensing limiter.

In operation, catheter 80 is placed within the vascular system and tip electrode 54 is arranged for ablating the target tissue. By virtue of its positioning in physical contact with tip electrode 54, PTC device 56 is in contact with rapidly flowing blood through the vascular system. The blood flowing by PTC device 56 will act as heat sink removing some of the heat generated by PTC device 56. This cooling effect allows PTC device 56 to tolerate a slightly higher level of current before exhibiting a very high resistance than would be possible if PTC device 56 were not being cooled. Moreover, since the surrounding blood effectively cools PTC device 56, PTC device 56 will not stay in a very high resistance state permanently after a current limit condition has been reached. Once catheter 80 is properly positioned within the vascular system, RF power is delivered to tip electrode 54 from the external power source. With tip electrode 54 in contact with the target tissue, the RF power is delivered to the target tissue with the system circuit being completed through backplate 69. As the temperature of the target tissue rises, so too does the temperature of PTC device 56 because it is in thermal contact with tip electrode 54. The target tissue will continue to be ablated until the temperature at the electrode/tissue junction rises to a level which causes PTC device 56 to change into a higher resistance state. Assuming that RF generator 66 is programmed to allow a moderate resistance change, the amount of current to tip electrode 54 will be automatically regulated to keep the temperature at the electrode/tip junction at an optimal level.

Figure 6:
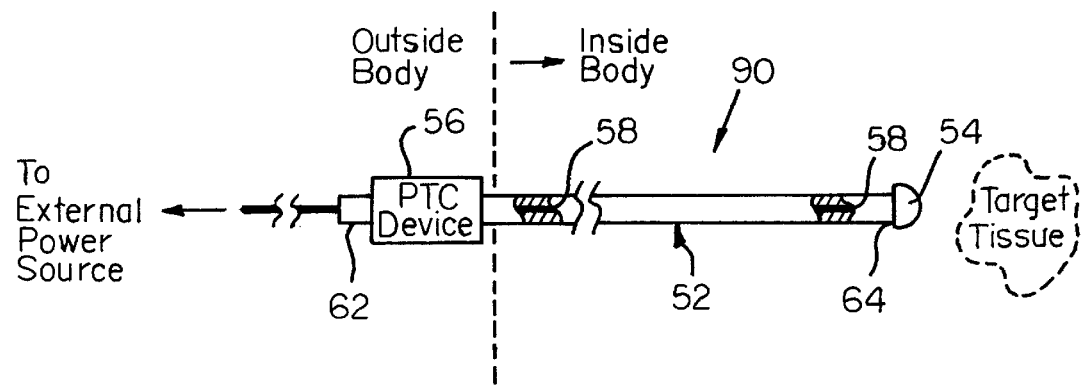
FIG. 6 is an alternative embodiment of a temperature and current limited ablation catheter according to the present invention.

In another embodiment of the present invention, which is illustrated in FIG. 6, catheter 90 is provided which has substantially the same features and attributes as catheter 50 of the present invention, except that catheter 90 includes PTC device 56 at proximal end 62 of catheter so that the PTC device remains outside of the body of the patient during an ablation procedure.

Operating catheter 90 with this arrangement allows PTC device 56 to operate as a pure current limiter with no temperature sensing characteristics. In addition, since PTC device 56 is not at the distal end of catheter 90, construction of catheter 90 is greatly simplified and permits distal end 64 of catheter 90 to be formed with a smaller diameter tip which is useful for insertion into small regions of the vascular system. Of course, the PTC device is still electrically connected to the single conductor 58, although being located at proximal end 62 of catheter body 52.

Figure 7:
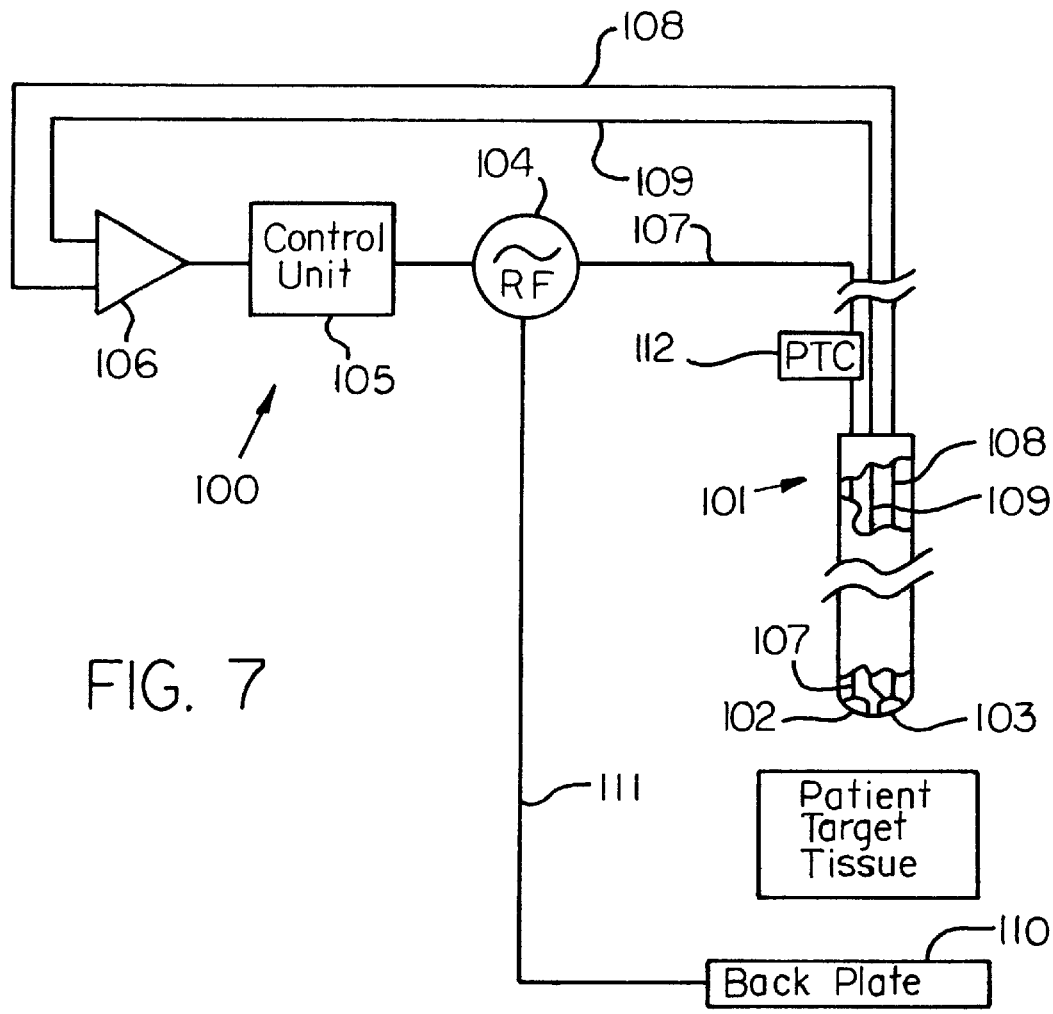
FIG. 7 is a further alternative embodiment of a temperature and current limited ablation catheter according to the present invention.

FIG. 7 illustrates a further alternative embodiment of the present invention. In this embodiment, an ablation system 100 is provided. Ablation system 100 contains a catheter 101 having a tip electrode 102 and a thermocouple 103 connected to the distal end of catheter 101. System 100 also includes an RF generator 104, a control unit 105 and an amplifier 106. Electrode 102 is connected to RF generator 104 through a single conductor 107. Thermocouple 103 is connected to RF generator 104 through control unit 105 and amplifier 106 via a pair of conductors 108, 109. A backplate 110 is also connected to RF generator 104 via conductor 111 to provide a return path for the current. A PTC device 112 is electrically connected adjacent tip electrode 102 via conductor 107. It should be noted that PTC device 112 can be located remotely from tip electrode 102, similar to the embodiment of catheter 90 (see FIG. 6) or in direct thermal contact with tip electrode 102, similar to the embodiment of catheter 80 (see FIG. 5). In this embodiment, temperature can be precisely monitored by combining the standard thermocouple temperaturelimiting arrangement while still providing fail-safe current and temperature shutdown limiting characteristics by use of the PTC device 112. This embodiment maximizes the temperature regulating characteristics of the ablation catheter.

Figure 8:
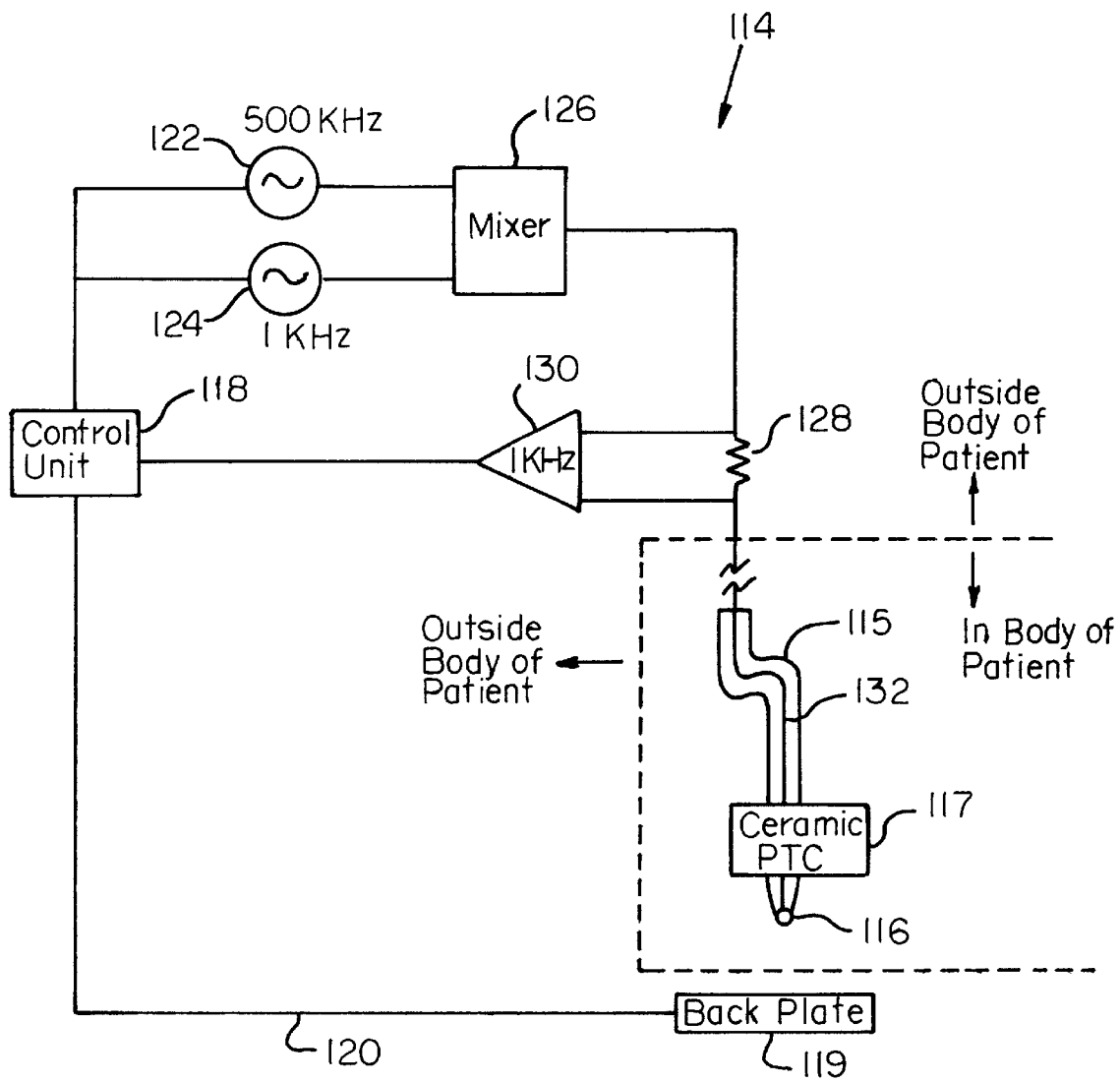
FIG. 8 is yet another alternative embodiment of an ablation catheter of the present invention using two frequencies.

FIG. 8 illustrates a further alternative embodiment a catheter ablation system 114 according to the present invention in which two frequencies are used for ablation. Ablation system 114 includes a catheter 115, tip electrode 116, a ceramic PTC device 117, a control unit 118 and a conductive backplate 119 connected via conductor 120. System 114 further includes a 500 kHz RF signal generator 122, 1 kHz signal generator 124, a frequency mixer 126, as well as a current sampling resistor 128 and frequency selective amplifier 130 tuned to 1 kHz. Ceramic PTC device 117 and tip electrode 116 are electrically connected via conductor 132 and are embodied in a catheter structure in accordance with the other embodiments of the present invention shown in FIGS. 3–7.

As shown in FIG. 8, system 114 uses two frequencies, namely 500 kHz and 1 kHz mixed via mixer 126 and delivered through current sampling resistor 128, ceramic PTC device 117 and tip electrode 116. The voltage drop across the sampling resistor 128 is amplified by frequency selective amplifier 130 which is tuned to 1 kHz. This amplification produces a signal flowing through conductor 132 that is indicative of the current flow at the low frequencies. In this system, if the temperature rises at ceramic PTC device 117, then its impedance at low frequencies goes up dramatically. This relationship results in a decreased current flowing to tip electrode 116 with the output from amplifier 130 decreasing as a result of this sensed impedance change causing the control unit to reduce the 500 kHz output. This approach allows the precise monitoring of temperature along with the use of an intrinsic current and temperature limiting mechanism, all accomplished with the single wire conductor 132 which simplifies the catheter construction.

Figure 9:
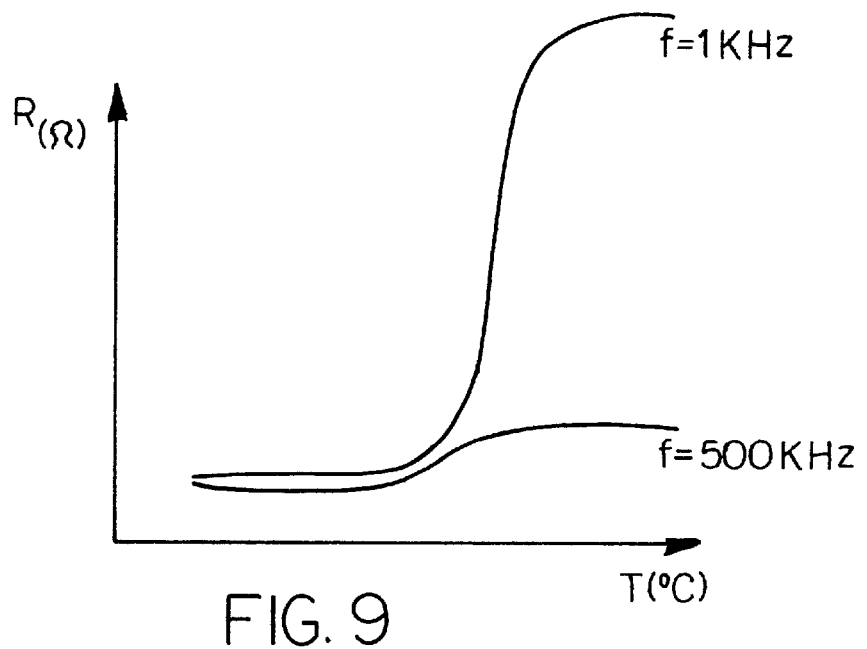
FIG. 9 is a graph illustrating a resistance and temperature relationship of a ceramic PTC device at multiple frequencies.

Catheter ablation system 114, as shown in FIG. 8, takes advantage of the unique properties of ceramic PTC devices which are very capacitive. The resistance of ceramic PTC devices increases very little in response to temperature changes when the ceramic PTC devices are run at high frequencies. This behavior results from the capacitive coupling across the grain boundaries in the ceramic composition of the PTC devices. This relationship is shown in FIG. 9, which is a graph illustrating a resistance and temperature relationship of a ceramic PTC device operating at frequencies of 1 kHz and 500 kHz. As can be seen, in the low frequency range a dramatic increase in resistance occurs as temperature increases while at higher frequency range, very little increase in resistance occurs with the increase in temperature.

Yet another use of the present invention is linear lesion ablation catheters. Such catheters are very long which results in a high current density at the ends of the catheter thereby generating hot spots of excessive temperature. By using a PTC device of the present invention, current could be limited at the hot spots at the ends of the long catheter by converting the ends of the linear lesion catheters to small ring tip electrodes in combination with the PTC approach. A variant on this design would include using multiple PTC devices on each end of the long catheter.

An ablation catheter of the present invention incorporating a positive temperature coefficient conductor provides numerous advantages in radio frequency ablation. The PTC device provides a built in fail-safe current limiter to avoid over-ablating the target tissue thereby protecting the patient, while insuring effective ablation with the catheter by preventing coagulation adherence to the catheter electrode tip and damage to the catheter and patient from overheating. Use of the PTC device to limit current and/or temperature at an ablation site within a vascular system greatly simplifies the task of temperature regulation which was previously provided by thermocouple-type systems.

Although the present invention has been described with reference to preferred embodiments, workers skilled in the art will recognize that changes may be made in form and detail without departing from the spirit and scope of the invention.

What is claimed is:

1. A radio frequency ablation system comprising:

an elongate flexible catheter including an electrical conductor having a proximal end and a distal end;

an electrode electrically connected to the distal end of the conductor;

a ceramic-type positive temperature coefficient (PTC) device electrically connected between the proximal end of the conductor and the electrode, a control unit;

a frequency mixer;

a low frequency generator and a high frequency generator connected in parallel to and extending between the control unit and the frequency mixer;

a resistive component electrically connected between the frequency mixer and the ceramic-type PTC device;

a frequency selective amplifier having an output connected to the resistive component and an inlet connected to the control unit; and a conductive plate electrically connected to the control unit for contacting a patient.

2. The ablation system as in claim 1, wherein the PTC device is adjacent the electrode.

3. The ablation system as in claim 1, wherein the conductor comprises a single conductor wire.

4. The ablation system as in claim 1, wherein the PTC device is a ceramic-type PTC device.

* * * * *